United States Patent [19]

Howarth

[11] 3,965,356

[45] June 22, 1976

[54] APPARATUS FOR MEASURING A PREDETERMINED CHARACTERISTIC OF A MATERIAL USING TWO OR MORE WAVELENGTHS OF RADIATION

[75] Inventor: John J. Howarth, San Jose, Calif.

[73] Assignee: Measurex Corporation, Cupertino, Calif.

[22] Filed: May 29, 1975

[21] Appl. No.: 581,836

Related U.S. Application Data

[63] Continuation-in-part of Ser. No. 573,173, April 30, 1975, abandoned, which is a continuation of Ser. No. 475,628, June 3, 1974, abandoned.

[52] U.S. Cl. .............................. 250/343; 250/226; 250/571; 250/578
[51] Int. Cl.² ...................... G01N 21/26; G01J 3/34
[58] Field of Search ............ 250/343, 571, 578, 226

[56] References Cited
UNITED STATES PATENTS 3,177,757   4/1965   Polanyi ........................... 250/226 X

*Primary Examiner*—Alfred E. Smith
*Assistant Examiner*—T. N. Grigsby
*Attorney, Agent, or Firm*—Flehr, Hohbach, Test, Albritton & Herbert

[57] ABSTRACT

Measuring apparatus is used as a control element to maintain the correct ratio of chlorine to pulp in a bleach plant. Two diffusing windows are used; one to randomly radiate electromagnetic energy into the pulp and the other to receive radiation from the bulk of the pulp and reradiate it. Two bands of radiation are examined; one in the visible and the other in the infrared. Rather than using a conventional beam splitter, two detection systems, differing only in their spectral pass band, are used. Their optical axes converge in the center of the receiving window so that identical images of the receiving window can be projected on each of the detectors. The detector system allows the use of interference type filters which require sensibly parallel radiation. In addition to sensing the brightness of pulp, which is affected by the amount of chlorine, the above apparatus is useful for concurrently measuring opacity, moisture content, and basis weight of a moving sheet. A single sided moisture gauge is also provided which eliminates the effects of flutter.

9 Claims, 7 Drawing Figures

FIG. 2-A

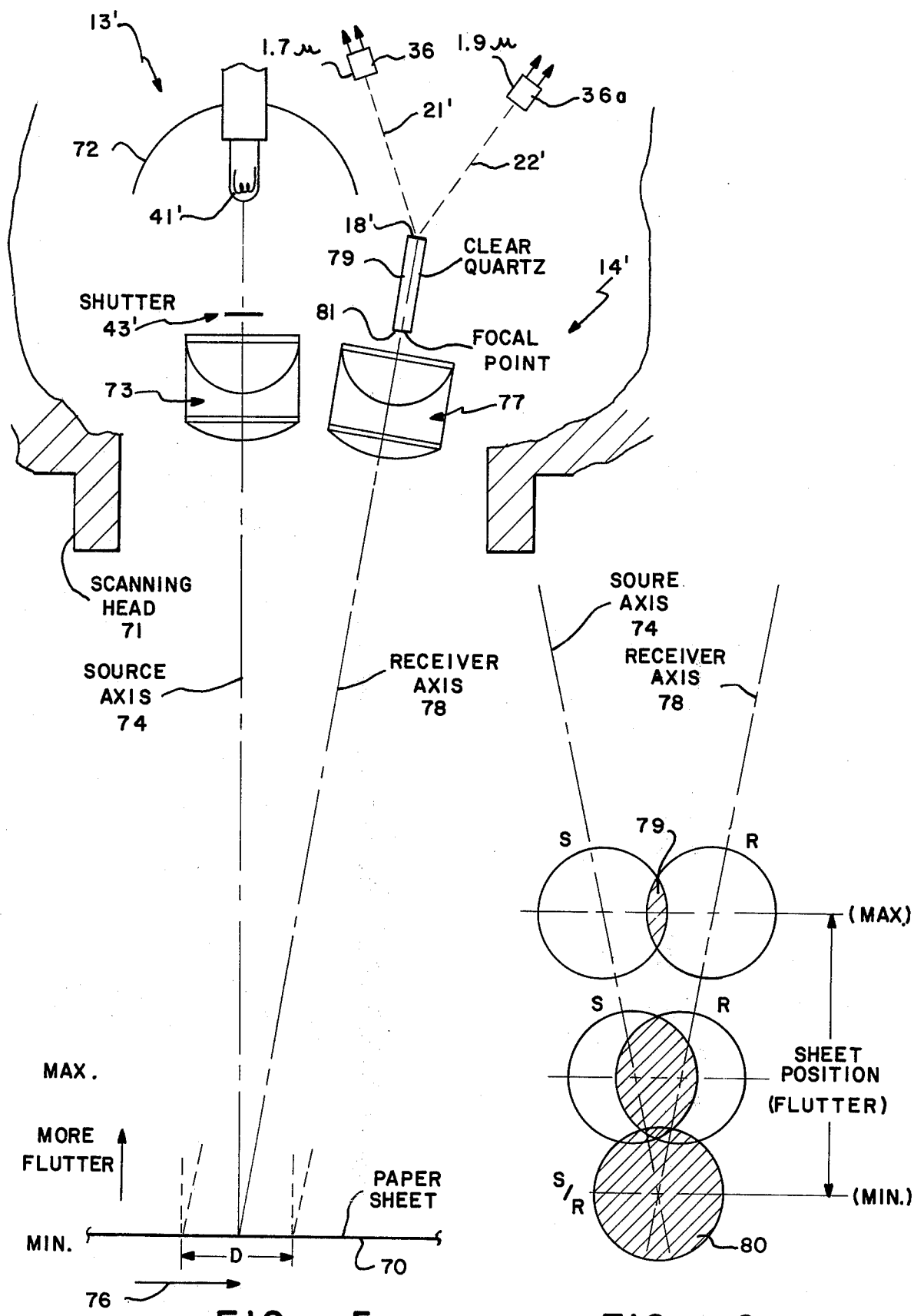

APPARATUS FOR MEASURING A PREDETERMINED CHARACTERISTIC OF A MATERIAL USING TWO OR MORE WAVELENGTHS OF RADIATION

CROSS REFERENCE TO RELATED APPLICATIONS

This application is a continuation in part of application Ser. No. 573,173 now abandoned, filed Apr. 30, 1975, in the name of the present inventor, which application is a continuation of application Ser. No. 475,628 now abandoned, filed June 3, 1974, in the name of the present inventor and assigned to the present assignee.

BACKGROUND OF THE INVENTION

The present invention is directed to apparatus for measuring a predetermined characteristic of a material in sheet or bulk form using two or more wavelengths of radiation; and more particularly, material moving in a pipeline such as paper pulp where a ratio of received radiation of two wavelengths provides a measurement.

In the paper making field, the measurement of the paper material by a ratio measurement is well known. For example, one wavelength is utilized as a reference which is relatively unaffected by the characteristic being measured and the other is the actual sample measurement. Naturally, the choice of these two wavelengths or wavelength bands is critical. Normally the best choice for a reference band is as close as possible to the measurement of sample band. In order to separate both the reference and sample wavelengths efficiently, a beam splitter has been used. This is unsatisfactory in many applications since the cutoff frequencies of the beam splitter are not sharp. This is especially troublesome where the wavelengths of interest are close to each other. In the paper making art, for example, critical wavelengths for reference and sample wavelengths for the measurement of moisture are in the range of 1.7 to 1.9 microns and known beam splitters are difficult to manufacture in this wavelength range. In addition if more than two wavelengths are used, beam splitters are very cumbersome. They are also critical with regard to sensitivity contours.

Another prior art technique for receiving and separating multiwavelength radiation for the purpose of measurement is the use of a diffusing plate to spread radiation evenly to several detectors. Here the radiation from plate to detectors is, by design, diffused, arriving at a wide variety of angles. Only absorbing body type filters can be used in this arrangement which are limited in bandwidth and band center characteristics. The versatile interference narrow bandpass type filters require nearly parallel radiation. This, of course, is not provided by the diffusing plate type apparatus above.

Where it is desired to utilize a single sided gauge for the measurement of moisture in moving sheet material, the use of a single detector with spinning filter wheels for the 1.7 and 1.9 micron wavelengths has been suggested. Because of the necessary time lapse the single detector is actually looking at two different portions of the moving material. If two detectors with a beam splitter are used, the splitter is sensitive to the flutter of the paper and other spatial effects.

OBJECTS AND SUMMARY OF THE INVENTION

It is, therefore, an object of the present invention to provide an improved apparatus for measuring a predetermined characteristic of a material using two or more wavelengths of radiation where such wavelengths may be placed in any desired portion of the electromagnetic spectrum and separated by appropriate filtering.

In accordance with the above object, there is provided apparatus for measuring a predetermined characteristic of a material using two or more wavelengths of radiation including a radiation source for emitting radiation having a plurality of wavelengths. A diffusing window receives at least a portion of the radiation after impinging upon the material and reradiates the received radiation. A plurality of radiation detector means each includes a filter centered around one of the plurality of wavelengths with each of the detector means having an optical axis. The optical axes of the detector means converge at substantially the same point in proximity to the diffusing window whereby each detector means receives substantially the same image of reradiation.

BRIEF DESCRIPTION OF THE DRAWINGS

FIG. 2A is a detailed cross sectional view illustrating the structural assembly of a portion of FIG. 2;

FIG. 5 is a greatly simplified optical schematic of another embodiment of the invention; and FIG. 6 is an optical diagram useful in understanding the embodiment of FIG. 5.

DETAILED DESCRIPTION OF THE PREFERRED EMBODIMENTS

The present invention finds preferred usage in one embodiment as a chlorination sensor at the chlorination tower or premixer of the bleach portion of a paper making plant. The sensor in its broad aspects is disclosed and claimed in a copending application in the name of John J. Howarth, the present inventor, entitled "Optical Reflectance Gauge and Method Therefor," filed Jan. 14, 1974, Ser. No. 433,269, now abandoned in favor of continuation application Ser. No. 576,543, filed May 12, 1975.

Figure 1:
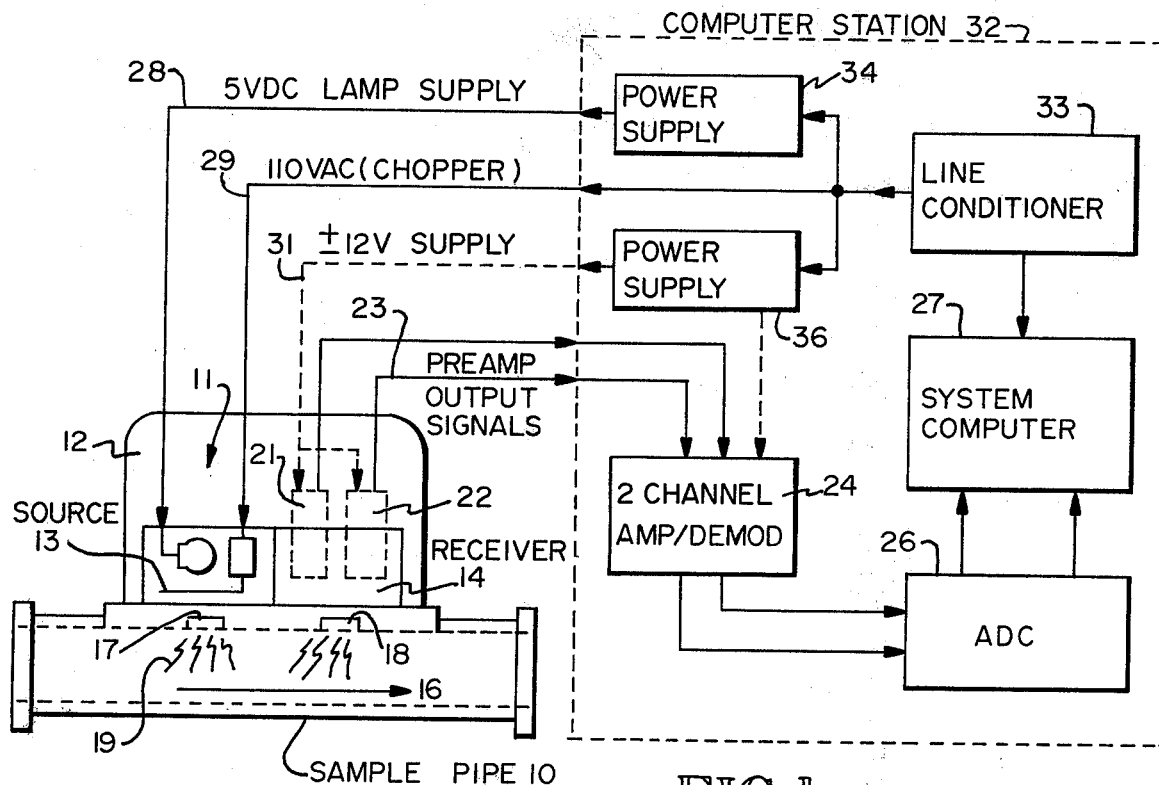
FIG. 1 is a block diagram illustrating the measuring environment of the present invention.

As illustrated in FIG. 1, such chlorination sensor is located along a pipeline 10 which has mounted on it the chlorination sensor 11 in a sealed enclosure 12. The sensor 12 includes a source portion 13 and a receiver portion 14. In general, source 13 provides a wide spectrum of radiation which is coupled to the material 16 flowing in pipe 10 through a window 17. Radiation detector or receiver 14 is also coupled to material 16 through a window 18 which is displaced in distance from window 17. The windows 17 and 18 are preferably of translucent quartz to provide in the case of transmission window 17 full diffusion of the source radiation into material 16 as shown at 19 and in the case of receive window 18 a solid half angle of received radiation which is reradiated and detected by a sample radiation detector 21 and a reference radiation detector 22.

The signals from radiation detectors 21 and 22 are coupled on the lines 23 to a two channel amplifier demodulator 24. In a manner well known in the paper making art in conjunction with moisture measurement, the sample and the reference signals are ratioed, converted to a digital value in analog to digital converter 26 and coupled to the system computer 27 for further use. The reference wavelength received by detector 22 is in the wavelength band of .85–.95 microns greater and the sampled wavelength received by detector 21 encompasses the visible range of .45 to .65 microns. The foregoing wavelengths are merely typcial and, for example a reference band of .85–9 microns and a sample band of .5–.7 microns may be used. The reference wavelength is only slightly affected by the change of reflectance of the material due to chlorination whereas the sample wavelength is highly sensitive. In effect, the chlorination sensor is also a brightness monitor since the greater the amount of bleaching the more orange the pulp appears.

Chlorination sensor 11 also has the appropriate voltage supplies which includes a 5 volt dc lamp supply on line 28 to radiation source 11, a 110 volt ac supply on line 29 which drives a chopper to provide for greater circuit stability and a 12 volt supply on line 31 for the receiver portion 14. In the computer station 32 which includes system computer 27 and the other electronics of the system, a line conditioner 33 supplies the appropriate voltages through power supplies 34 and 36.

Figure 2:
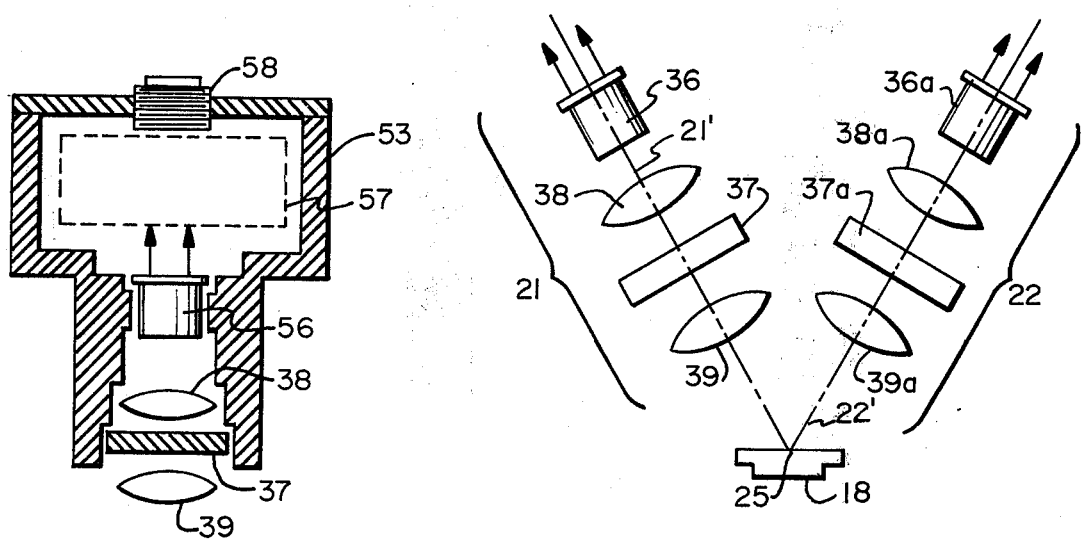
FIG. 2 is an optical schematic of the detector assembly of the present invention.

FIG. 2 illustrates detectors 21 and 22 in greater detail. Each has an optical axis, respectively 21' and 22', which converge at substantially the same point 25 in proximity to the diffusing window 18. The axes are side elements of a common cone. Thus each of the detector means 21 and 22 receives substantially the same image of reradiation from the half angle radiation of the diffusing window 18. This compensates for any shadowing of the window and provides a more accurate measurement. Detector means 21 includes a filter 37 of the absorbing body type the bandpass being centered around the sample wavelength band of .45–.65 microns. The optical system includes convex lenses 38 and 39 to provide for parallel radiation on optical axes 21'. Detector means 22 includes a narrow bandpass filter 37a of the optical interference type with a bandpass centered on the sample wavelength band of .85–.95 microns. Convex lenses 38a and 39a are located on optical axis 22' to provide for substantially parallel radiation to pass through filter 37a. This is, of course, required for the narrow bandpass filter to function adequately.

Although interference and body type filters are used in the preferred embodiment, other filter combinations may be used depending on the wavelengths of interest. Body type filters are suitable only for the visible wavelengths and are wideband. Interference filters are narrow band and suitable for both visible and infrared wavelengths. Thus for the measurement of moisture interference filters centered at 1.7 and 1.9 microns would be used; for an opacity measurement a body type filter of .4–.7 microns; and for fiber basis weight an interference filter of 2.1 microns.

In accordance with the invention several different filter types and bandpasses can be arranged in a package with their optical axes all lying in a common cone. Thus, measurements of several different characteristics of a moving material may be made concurrently.

Figure 3:
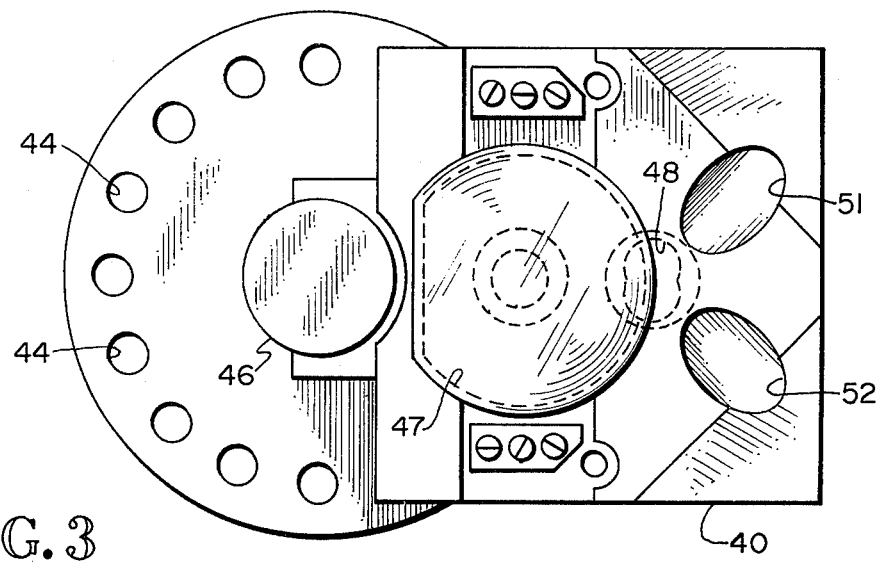
FIG. 3 is an elevational view of a portion of FIG. 1 embodying the present invention.
Figure 4:
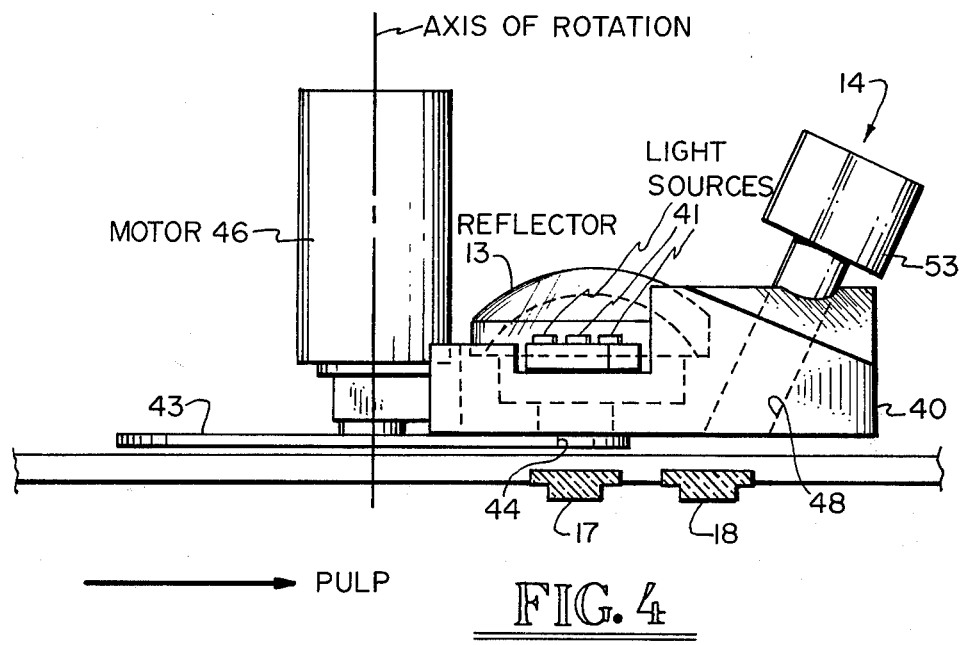
FIG. 4 is a top view of FIG. 3.

Referring to both FIGS. 3 and 4, this illustrates the overall chlorination sensor 11 shown in FIG. 1. The radiation source 13 includes light sources 41 which are aimed toward to a dome-shaped reflector 42 to be reflected toward window 17. This light is interrupted by a chopper wheel 43 having aperatures 44 cut therein and which is driven by a motor 46. Light sources 41 are mounted in a circular cavity 47.

Receiver portion 14 includes the drill holes 51 and 52 in a supporting block 40 both of which converge at window 18 through the aperture 48 in block 40. Thus, the drill holes 51 and 52 support the housing 53 so that the optical axes of the detector means are aligned to converge at substantially the same point in proximity to diffusing window 18. One detector housing 53 which is illustrative of detector means 21 is shown inserted in the drill hole 52 in FIG. 4.

Thus, the present invention in the foregoing embodiment has provided improved apparatus for measuring a predetermined characteristic of a material by the use of two or more wavelengths. With the elimination of a beam splitter it is possible to combine receivers working in widely differing regions of the electromagnetic spectrum as, for eample, combining both infrared measurements for moisture as well as visible measurements for opacity of moving paper sheet material. More than two optical receiver/detector packages can easily be arranged symmetrically around the diffusing window. All that is required is that the optics provide an identical image of the diffusing window focused on it. In fact, it is not necessary to focus the window on the detector as long as the optical path in each receiver package is geometrically identical. Such identical optical channels eliminate effects due to window fouling.

FIG. 5 illustrates another embodiment of the invention which provides for a single sided moisture gauge. In other words, the entire gauge may be located on one side of a moving sheet of material indicated as paper sheet 70. This is in contrast to a standard scanning type moisture gauge which has both an upper and lower scanning head as, for example, illustrated in U.S. Pat. No. 3,675,019. A single sided moisture gauge is advantageous in many environments; these include where the material may be too thick for transmission type measurements such as with ceiling tile, or where the material exhibits heavy attenuation of any transmissive radiation such as the wet end of the paper making process. In addition, space may be limited where there is space for only a single scanning head and lastly, it may be less expensive in many installations to provide a single sided moisture gauge. The gauge illustrated in FIG. 5 as will become apparent is also useful for measuring weight per unit area and the surface properties of many materials; for example, the polyethelene laminated onto paper to form milk cartons.

Referring now to FIG. 5, a scanning head 71 is normally retained on a carriage and scanned across the moving sheet 70 as is well known in the art. Head 71 includes a radiation source 13' and a radiation receiver 14'. Radiation source 13' includes a source of light 41', for example a tungsten filament which has both visible and infrared radiation, a reflector 72 which reflects and focuses the light from 41' at the shutter location 43' and a lens system 73 which has a source axis 74 and essentially a beam of radiation which when it intercepts the paper sheet 70 provides a beam spot of diameter D as indicated. Paper sheet 70 is moving in the direction as indicated by arrow 76 and as is typical in the paper making process will flutter; that is, it will move in a direction normal to the plane of the sheet between a minimum and maximum position. The effect of such flutter must, of course, be accommodated in the measuring procedure. Receiver portion 14' includes a lens system 77 which provides the receiver axis 78 which coincides with source axis 74 when the paper is at its minimum flutter point as indicated. In addition, the lens system 77 also provides substantially the same beam spot with diameter D. Referring briefly to FIG. 6, the coincidence beam spots are indicated at 78.

Now briefly comparing FIG. 2 with FIG. 5 the diffusing window 18' indicated in FIG. 2 is effectively provided by the roughened end 18' of the clear quartz rod 79. This lies along the receiver axis 78 and in addition includes a second roughened end 81 which is at the focal point of the lens system 77. The ends 81 and 18' provide in essence a diffusing window which is equivalent to the window 18 of FIG. 2. The detector assemblies identical to those of FIG. 2 lie along the optical axis 21' and 22' and in the case of the measurement of moisture as in this embodiment one detector would include a filter sensitive to a 1.7 micron wavelength as indicated and the other detector a filter sensitive to the 1.9 micron wavelength. The ratio of these two detector readings thus would provide an accurate measurement of moisture in the paper sheet 70.

Referring now to FIG. 6, when flutter occurs in the sheet 70 it is apparent that the common portion of the sheet seen by the source and receiver changes as the sheet moves in a direction normal to its plane. In addition to producing undesirable spatial effects this attenuates the total signal which in turn causes errors in the final output ratio of the two signals due to nonlinearities in the detector response. However, such attenuation is compensated for by the present invention which takes advantage of the fact that light intensity is proportional to the area indicated by the cross-hatched portions of FIG. 6 as seen by the receiver and inversely proportional to the distance squared between the sheet material and the receivers. Thus as flutter increases toward a maximum, the coincident portion 79 of the two optical axes 74 and 78 reaches a minimum, but the sheet is moved closer to receivers 14' to thereby maintain the light intensity relatively constant.

The other principal problem of flutter relates to the spatial effect caused thereby. One manifestation of this can be seen from FIG. 6. That is, the image of the sheet seen by the receiver not only changes size, but moves from right to left. This effect has a very serious impact on dual wavelength gauges with two detectors since it is nearly impossible for both detectors to be perfectly uniform and be perfectly aligned. However, in accordance with the present invention light transmission means in the form of a clear quartz rod 79 receives the spatially affected light at its end 81 and mixes individual light rays so that light coming from window 18' appear to the detectors as if it came from a uniform source. The reflected light rays from sheet 70 are only slightly attenuated so that the signal still remains above the noise level but are diffused enough to eliminate any unwanted spatial effects. Such spatial effects in addition to that produced by the flutter may also include, for example, those effects produced by the structural inhomogeneity of the material being measured.

What is claimed is:

1. Apparatus for measuring a predetermined characteristic of a material using two or more wavelengths of radiation comprising: a radiation source for emitting radiation having a plurality of wavelengths; a diffusing window for receiving at least a portion of said radiation after impinging upon said material and for reradiating said received radiation; a plurality of radiation detector means each including a filter respectively centered around one of said plurality of wavelengths each of said detector means having an optical axis; means for supporting said plurality of detector means for aligning said optical axes to converge at substantially the same point in proximity to said diffusing window whereby each detector means receives substantially the same image of reradiation.

2. Apparatus as in claim 1 where at least one of said detector means includes a filter of the narrow band interference type.

3. Apparatus as in claim 2 where said detector means includes lens means for providing substantially parallel radiation through such filter.

4. Apparatus as in claim 2 where said predetermined characteristic is chlorination and said narrow band filter is centered around .85–.95 microns and together with a second body type filter for another detector means centered around .45–.65 microns.

5. Apparatus as in claim 1 where said optical axes are elements of a common cone configuration and each of said detector means includes preamplifier means respectively located in said axes.

6. Apparatus as in claim 1 where said material is moving sheet material having filter between minimum and maximum limits, said radiation source having an optical axis, together with lens means associated with said diffusing window for providing an optical axis which substantially coincides with said source axis when said sheet material is at its minimum limit, radiation from said source being reflected from said sheet material and received along said diffusing window optical axis.

7. Apparatus as in claim 6 together with light transmission means coincident with said diffusing window optical axis for slightly diffusing said received radiation whereby spatial effects are eliminated.

8. Apparatus as in claim 7 where said light transmission means is a clear quartz rod having at least one end roughened to serve as said diffusing window.

9. Apparatus as in claim 1 where said radiation source has an optical axis, together with lens means associated with said diffusing windows for providing an optical axis along which radiation from said material, together with lens means associated with said diffusing window for providing an optical axis which substantially coincides with said source axis when said sheet material is at its minimum limit, radiation from said source being reflected from said sheet material and received along said diffusing window optical axis.

* * * * *

UNITED STATES PATENT AND TRADEMARK OFFICE
CERTIFICATE OF CORRECTION

PATENT NO. : 3,965,356
DATED : June 22, 1976
INVENTOR(S) : John J. Howarth

It is certified that error appears in the above-identified patent and that said Letters Patent are hereby corrected as shown below:

Claim 6, line 2, delete "filter" and substitute therefor

--flutter--

Cancel Claim 9.

Signed and Sealed this

Seventeenth Day of January 1978

[SEAL]

Attest:

RUTH C. MASON
*Attesting Officer*

LUTRELLE F. PARKER
*Acting Commissioner of Patents and Trademarks*